United States Patent [19]

Murphy, Jr.

[11] Patent Number: 4,571,988
[45] Date of Patent: Feb. 25, 1986

[54] APPARATUS AND METHOD FOR MEASURING VISCOSITY

[75] Inventor: Robert J. Murphy, Jr., Bellaire, Tex.

[73] Assignee: NL Industries, Inc., New York, N.Y.

[21] Appl. No.: 631,237

[22] Filed: Jul. 16, 1984

[51] Int. Cl.⁴ ............................................. G01N 11/14
[52] U.S. Cl. ..................................................... 73/60
[58] Field of Search ....................................... 73/60, 59

[56] References Cited

U.S. PATENT DOCUMENTS 3,435,666 4/1969 Fann ........................................ 73/60

FOREIGN PATENT DOCUMENTS 672380 10/1963 Canada ..................................... 73/59

Primary Examiner—S. Clement Swisher
Assistant Examiner—Joseph W. Roskos
Attorney, Agent, or Firm—Browning, Bushman, Zamecki & Anderson

[57] ABSTRACT

The present invention is directed to an apparatus and method for measuring the viscosity of a fluid. This apparatus and method is particularly useful for the measurement of the viscosity of a liquid in a harsh environment characterized by high temperature and the presence of corrosive or deleterious gases and vapors which adversely affect conventional ball or roller bearings. The apparatus and method of the present invention employ one or more flexural or torsional bearings to suspend a bob capable of limited angular motion within a rotatable sleeve suspended from a stationary frame.

14 Claims, 7 Drawing Figures

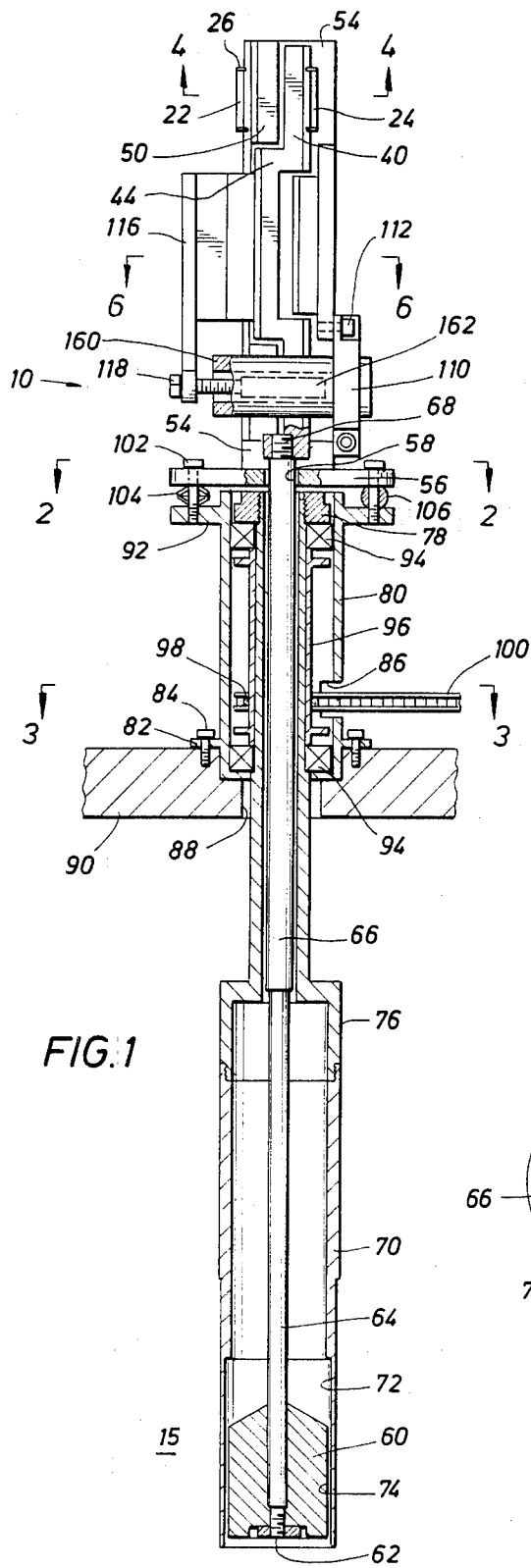

APPARATUS AND METHOD FOR MEASURING VISCOSITY

STATEMENT OF GOVERNMENT RIGHTS

The government of the United States of America has rights in this invention pursuant to Government Contract No. DE-AC-04-77ET 27144 awarded by the U.S. Department of Energy.

BACKGROUND OF THE INVENTION

1. Field of the Invention

The present invention generally relates to an apparatus and method useful for measuring the viscosity of a fluid. The present invention is particularly useful for measuring the viscosity of a liquid in an environment which is corrosive or harmful to typical ball or roller bearings. More particularly, the present invention relates to an apparatus and method employing flexural or torsional bearings and useful for making viscosity measurements in environments harmful to typical ball or roller bearings.

2. Description of the Background

It is desirable to determine the viscosity of fluids, particularly liquids, under a variety of conditions of temperature, pressure, atmosphere and the like to simulate the expected working environment in which the fluid will be employed. The liquids to be tested and/or the environment in which the tests are performed may be corrosive or at least harmful or deleterious to the testing equipment. For example, it is desirable to determine the viscosity of drilling fluids under conditions simulating the actual borehole conditions to which the fluids will be subjected. It is not uncommon to encounter temperatures in excess of 400° F. and pressures in excess of 10,000 psi in deep well bore operations. Accordingly, in order to properly evaluate drilling fluids useful in deep drilling operations, it is desirable to obtain viscosity measurements conducted under these harsh conditions. In fact, it is desirable to conduct these tests under even more extreme conditions, e.g., at temperatures in excess of 700° F. and at pressures in excess of 20,000 psi. Further, it is often desirable to perform these tests in the presence of corrosive fluids, e.g., hydrogen sulfide, which are often encountered in the drilling operation.

Apparatus for measuring the viscosity of liquids includes conventional rheometers. These conventional rheometers generally comprise a cylindrical bob suspended within a concentric tubular sleeve for immersion in the fluid to be tested. These devices further comprise a means for rotating the sleeve at a known velocity. Finally, these devices include a means for measuring the drag transferred to the suspended bob from the fluid in the annulus between the rotating sleeve and suspended bob. The bob and sleeve are suspended from a stationary frame, the bob being suspended by conventional ball or roller bearings. The condition and lubrication of these bearings is extremely important to the proper functioning of conventional rheometers. It will be appreciated by those skilled in the art that the lubrication and condition of the suspension and bearing system is highly critical to precise and accurate measurement of the angular motion or torque imparted to the bob. These bearings suffer from many disadvantages, particularly when used in remote, corrosive or harmful environments. Conventional ball or roller bearings tend over time to become pitted or gummed up, resulting in inaccurate viscosity measurements and, eventually resulting in failure of the instrument. These problems are accelerated and accentuated in rheometers used to make accurate and precise viscosity measurements in remote, corrosive or harmful environments.

Accordingly, there has been a long felt but unfulfilled need within the testing industry for a rheometer-type apparatus and method for measuring the viscosity of a liquid without relying upon ball or roller bearings to facilitate the measured motion.

SUMMARY OF THE INVENTION

The present invention provides a new and improved apparatus and method for measuring the viscosity of a fluid. The apparatus and method of the present invention are particularly useful for measuring the viscosity of a liquid in a harsh environment characterized by conditions harmful or deleterious to conventional ball or roller bearings, e.g., at high temperatures and/or in the presence of corrosive vapors or gases. The present invention provides an apparatus and method for making fluid viscosity measurements employing flexural or torsional bearings to overcome the disadvantages of conventional ball or roller bearings.

A rheometer in accord with the present invention conveniently comprises a stationary frame from which a rotatable sleeve is suspended and includes a means for rotating the sleeve. Suspended within the sleeve is a bob capable of limited angular motion about the longitudinal axis of the sleeve. The device is constructed so that the bob and at least the portion of the sleeve near the bob may be immersed within the liquid, the viscosity of which is to be determined. The bob is suspended from the stationary frame by a flexural or torsional bearing which permits limited angular motion about its center of rotation. Finally, the device of the present invention comprises means for measuring the angular motion imparted to the bob by the liquid from the rotating sleeve. Given the known characteristics of the rheometer, this motion is proportional to the viscosity of the liquid.

In a presently preferred embodiment of the invention, the bob is rigidly attached to a movable frame which is suspended from a flexural bearing. In this embodiment, the angular motion imparted to the bob through the liquid is conveniently measured by measuring the motion of the movable frame relative to the stationary frame. Although this motion is measurable by any conventional means, e.g., visual or electronic devices, those skilled in the art will appreciate that a convenient remotely operated means, preferably an electrical motion sensing device, is particularly appropriate for a rheometer intended to be used in remote, harsh environments. Further, as with conventional rheometers, the exterior contour of the bob must closely approximate the interior contour of the sleeve near the bob so that the viscosity of the liquid is measurable by the transmission of motion from the sleeve to the bob. In a presently preferred embodiment of the invention, a plurality of cross-spring pivots form the flexural bearing. However, a device employing one or more flexural pivots or any other flexural or torsional bearing is clearly within the contemplation of the present invention.

The method of the present invention comprises suspending a rotatable sleeve from a stationary frame and suspending a bob, capable of limited angular motion about the longitudinal axis of the sleeve, within the sleeve through a flexural or torsional bearing from the stationary frame. The method further comprises immersing the bob and that portion of the sleeve near the bob in the liquid, the viscosity of which is to be determined, rotating the sleeve and measuring the angular motion imparted to the bob through the liquid. A presently preferred method comprises suspending the bob from a flexural bearing by a movable frame to which the bob is rigidly attached and measuring the angular motion imparted to the bob by measuring the relative motion between the movable frame and the stationary frame. Alternative embodiments of the present method comprise suspending the bob from a cross-spring pivot or from a flexural pivot. A presently preferred embodiment comprises measuring the angular motion with an electrical or electronic motion sensing device.

The apparatus and method of the present invention solve the long felt but unfulfilled need for a rheometer for measuring fluid viscosity in harsh environments. The apparatus and method of the present invention eliminate the ball or roller bearings from which the bob is conventionally suspended and which are particularly subject to the deleterious effects of harsh and corrosive environments, resulting in incorrectly measured viscosity and instrument failure. The apparatus and method of the present invention eliminate the conventional ball or roller bearings and employ therefor one or more flexural or torsional bearings to provide an accurate, rugged and improved rheometer particularly useful in harsh environments. These and other meritorious features and advantages of the present invention will be more fully appreciated from the following detailed description and claims.

BRIEF DESCRIPTION OF THE DRAWINGS

Other features and intended advantages of the present invention will be more readily apparent by the references to the following detailed description in connection with the accompanying drawings wherein:

FIG. 1 is an illustration in partial cross section of a rheometer in accord with the present invention incorporating a plurality of cross-spring pivots;

FIG. 2 is a cross-sectional illustration through the plane 2—2 of the rheometer of FIG. 1 illustrating the top of the mounting flange;

FIG. 3 is a cross-sectional illustration through plane 3—3 of the rheometer of FIG. 1 illustrating the means for rotating the rheometer sleeve;

FIG. 7 is an exemplary illustration of a theoretical cross-spring pivot in the relaxed and a torqued position.

Figure 4:
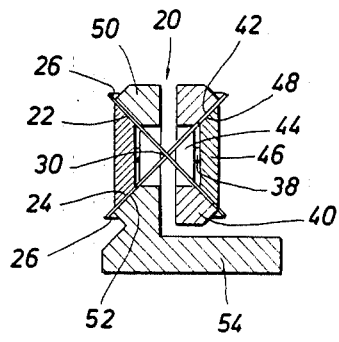
FIG. 4 is a cross-sectional illustration through the plane 4—4 of the rheometer of FIG. 1 illustrating a cross-spring pivot.

While the invention will be described in connection with the presently preferred embodiment, it will be understood that it is not intended to limit the invention to this embodiment. On the contrary, it is intended to cover all alternatives, modifications and equivalents as may be included in the spirit of the invention as defined in the appended claims.

DETAILED DESCRIPTION OF THE PREFERRED EMBODIMENT

Flexural and torsional bearings are bearings which flex or twist in an elastic member which supports the load. Flexural and torsional bearings are useful for applications in which only limited angular or translatory motions are required. Further, these bearings offer many useful advantages. Flexural and torsional bearings do not require a lubricant, are relatively unaffected by environment, e.g., dirt, temperature and the like, have no loose parts, have no wearing parts, withstand rough handling, do not gum up, withstand load reversals and operate with zero clearance. Accordingly, flexural and torsional bearings may advantageously be employed where one or more of the above features is advantageous.

Flexural bearings may be designed to permit limited angular or translatory motion about one or more axes. Of particular interest are simple flexural pivots and cross-spring pivots designed for limited angular rotation about a single axis. FIG. 7 of the drawings illustrates an exemplary cross-spring pivot 120 in the relaxed position and in a torqued position. Those skilled in the art will appreciate that a cross-spring pivot 120 is comprised of flexural strips 122, 124 crossed at 130. These strips are typically comprised of a strong, flexible and elastic material, e.g., spring steel or stainless steel. In the relaxed position, strips 122, 124 cross perpendicularly at 130 along an axis or center of rotation A. A first end of each strip 122, 124 is attached to a stationary frame 150. The opposite end of each strip 122, 124 is attached to a movable frame 140. The application of a force or torque to the movable frame 140 creates a load or moment resulting in limited angular motion about the axis or center of rotation A as illustrated. If the angular displacement $\theta$ is small, preferably less than about two degrees (2°), the cross-spring pivot may be employed to accurately determine the force or torque applied to the movable frame. Accordingly, the cross-spring pivot is advantageously employed in an apparatus for accurately determining force or torque.

The apparatus and method of the present invention provide a means for measuring the viscosity of a liquid employing one or more flexural or torsional bearings and particularly useful in a harsh environment where one or more of the features of flexural bearings listed above is advantageous. FIGS. 1-6 of the drawings illustrate a presently preferred embodiment of a rheometer in accord with the present invention. This system is particularly useful in the measurement of the viscosity of liquids in harsh environments characterized by high temperature and/or the presence of dirt, corrosive or deleterious vapors or gases or the like. Such a device is particularly useful for measuring the viscosity of drilling fluids and the like under conditions simulating the harsh borehole environment.

A presently preferred embodiment of a rheometer 10 in accord with the present invention for measuring the viscosity of a fluid 15 is illustrated in FIG. 1. The rheometer 10 comprises a stationary frame comprising a bearing support 54 extending above a support base 56. The support 54 is attached to the base 56 by any conventional means, e.g., threaded screws 108 extending upward through recessed bores in base 56 and into cooperating tapped bores in support 54. The stationary frame further comprises a sleeve support 80 conveniently of cylindrical configuration and having an upper flange 92 and a lower flange 82. In the illustrated embodiment, the support base 56 is attached to the sleeve support 60 of the stationary frame by a plurality of threaded screws 102 passing through bores in the support base 56 and into cooperating tapped bores in the flange 92. In the illustrated embodiment, the support frame is affixed to a base plate 90 by a plurality of threaded bolts 84 passing through bores in flange 82 and into cooperating tapped bores in the base plate 90. The base plate 90 is suspended by any conventional means (not shown) above the fluid 15.

The illustrated rheometer 10 further includes a tubular sleeve comprised of a lower sleeve 70 threadedly attached to an upper sleeve 76 which in turn is threadedly attached near its upper end to an annular support collar 78. This tubular sleeve passes through a bore 88 in the base plate 90 and is supported within the sleeve support portion 80 of the stationary frame by conventional ball or roller bearings 94 to permit rotation of the sleeve. Rigidly attached about the exterior of the sleeve 76 by any conventional means, e.g., a set screw, is a concentric drive sleeve 96 for imparting rotation to the sleeves 76 and 70. Those skilled in the art will appreciate that the drive sleeve 96 may be rotated by any convenient means. In the illustrated embodiment, the drive sleeve 96 includes sprockets 98 located about its periphery for cooperation with a chain 100 passing through an opening 86 in the sleeve support 80 of the stationary frame. The chain 100 is conveniently driven by a motor (not shown) capable of turning the sleeve 70 at speeds up to about 1200 rpm. The motor is conveniently attached to base plate 90.

The illustrated rheometer 10 further comprises a solid, cylindrical bob 60 having a recessed bore through its axis through which it is rigidly attached by a threaded screw 62 to the lower end of a rigid support rod 64. The rod 64 is attached at its opposite end to a concentric rod 66 passing through the sleeve 76 and a bore 58 in the support base 56. The rod 66 is threadedly attached at 68 to the lower end of the movable frame 44. The movable frame 44 is configured to cooperate with the bearing support 54 of the stationary frame.

It will be appreciated by those skilled in the art that the clearance between the exterior surface 74 of the bob 60 and the interior surface 72 of the sleeve 70 near the bob must be small in order for the rotation of the sleeve 70 to impart an angular motion to the bob 60 proportional to the viscosity of the intervening fluid 15. Accordingly, the bob 60 must be precisely aligned within the rotating sleeve 70 for proper operation. A convenient means of achieving the necessary alignment is illustrated at the juncture of the support base 56 and the flange 92 of sleeve support 80 of the stationary frame. If the support base 56 and flange 92 are interconnected at three points arranged in a triangular configuration, the support base 56 and supported apparatus, including the bob 60, may be leveled or aligned by many convenient means. For example, when attached by three threaded bolts 102 arranged in a triangular configuration, the support base 56 is easily leveled when one bolt 102 passes through a bore in a pivot ball 106 located between the support base 56 and the flange 92 and the remaining two bolts 102 pass through an adjustable spacer, e.g., bellville springs 104, located between the support base 56 and the flange 92. By adjusting the bolts 102 passing through the bellville springs 104, the support base 56 is leveled or adjusted to properly align the bob 60 within the rotating sleeve 70.

The rheometer 10 of the presently preferred embodiment includes two cross-spring pivots 20. The upper cross-spring pivot 20 is illustrated in cross section in FIG. 4 while the lower cross-spring pivot 20 is concealed behind motion detector core 160 in FIG. 1. The illustrated rheometer 10 is constructed to permit the use of at third cross-spring pivot 20 located between the first and second pivots and suspending the movable frame 44 from the bearing support 54 of the stationary frame in the approximate area of the detector rod support bracket 114.

Figure 5:
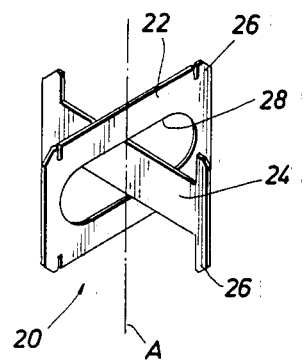
FIG. 5 is a perspective illustration of a cross-spring pivot assembly useful in a rheometer in accord with the present invention.

Referring to FIG. 5, the flexural strips used to form a cross-spring pivot 20 are illustrated. These flexural strips are constructed of any appropriate material having the necessary flexibility, elasticity and durability, e.g., spring steel, stainless steel, beryllium-copper alloys and the like. The flexural strip 22 conveniently comprises a generally rectangular strip having a symmetrically located hole 28 of generally oval configuration therein. The hole 28 must be of sufficient size to permit the insertion therethrough of the flexural strip 24 and the orientation thereof to produce the desired axis of center of rotation A. A cross-spring pivot 20 constructed in this manner permits flexure about the axis or center of rotation. A. When the angle of rotation is restricted to less than about two degrees (2°), the intersection 30 of the strips 22, 24 will not be appreciably shifted from the center of rotation A and the spring may be employed in an accurate force or torque measuring device. The flexural strips 22, 24 include tabs 26 near the ends thereof deformable to facilitate the mounting of the strips to the bearing support 54 of the stationary frame and to the movable frame 44.

Referring now to FIG. 4, the means by which the movable frame 44 is suspended from the bearing support 54 is illustrated. The bearing support 54 at each pivot includes two stationary pivot members 50 configured for contact with the crossed flexural strips 22, 24. Each pivot member 50 includes a face 52 for contact with a first end of one of the crossed flexural strips 22, 24. Similarly, the movable frame 44 at each pivot includes two movable pivot members 40, each having a face 42 for contact with the opposite end of flexural strips 22, 24. The flexural strips 22, 24 are secured in place by deformable tabs 26 and holding plates 46 having faces 48 for cooperation with faces 42, 52. The holding plates 46 are securely attached to frames 44, 54 by threaded screws 38 or other conventional means. This arrangement produces a cross-spring pivot having an axis of rotation A passing through the intersection 30 at which flexural strips 22, 24 cross when at rest.

Figure 6:
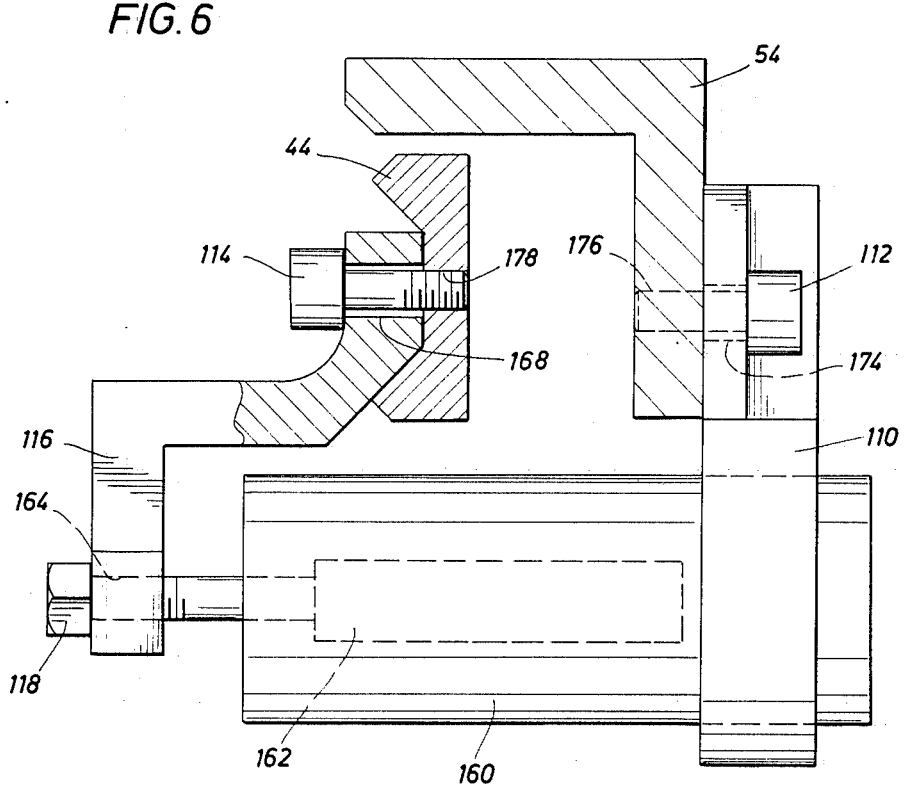
FIG. 6 is a cross-sectional illustration through the plane 6—6 of the rheometer of FIG. 1 illustrating the means for measuring the relative motion of the movable and stationary frames.

Finally, the rheometer 10 of the present invention comprises a means for measuring the angular motion imparted to the bob 60. In the illustrated rheometer 10 this motion is transferred from the bob 60 through ridigly attached rods 64 and 66 to the movable frame 44. Accordingly, the angular motion imparted to the bob 60 may be detected by measuring the motion of the movable frame 44 relative to the bearing support 54 of the stationary frame. Referring to FIG. 6, a convenient means for measuring this motion is illustrated. The presently preferred embodiment of rheometer 10 includes a conventional LVDT motion sensor. This motion sensor comprises a core 160 held by a support bracket 110 and rigidly attached to the bearing support 54 of the stationary frame by threaded bolt 112 passing through a bore 174 in the bracket 110 and into a tapped bore 176 in the bearing support 54. The LVDT motion sensor further comprises a movable rod 162 rigidly attached to a support bracket 116. The rod 162 is conveniently threaded to the end of a threaded bolt 118 passing through a bore 164 in the bracket 116 and configured to locate the rod 162 concentrically within the core 160. The support bracket 116 is attached to the movable frame 44 by threaded bolts 114 passing through bores 168 in the bracket 116 and into tapped bores 178 in the movable frame 44. Accordingly, the limited angular motion imparted to the bob 60 and transferred through the support rods 64, 66 to the movable frame 44 is transferred through the support bracket 116 to the rod 162 within the core 160 of the conventional LVDT motion sensor. Those skilled in the art will appreciate that the viscosity of the fluid 15 is easily determined by the detection of this motion together with a knowledge of the bob 60, the sleeve 70, the rotational velocity of the sleeve 70 and the characteristics of the cross-spring pivots 20.

Athough it is believed that those skilled in the art will clearly understand the method of the present invention, this method is briefly summarized below in relation to the operation of the illustrated rheometer 10. The method of the present invention comprises suspending a rotatable sleeve 70 from a bearing support 54 of a stationary frame and suspending a bob 60 capable of limited angular motion about the longitudinal axis of the sleeve 70 within the sleeve 70 from a flexural or torsional bearing 20. Further, the method of the present invention comprises immersing the bob 60 and that portion of the sleeve 70 near the bob within the fluid 15, the viscosity of which is to be measured. Finally, the method comprises rotating the sleeve 70 at a known velocity and measuring the angular motion imparted to the bob 60, e.g., by measuring the relative motion of the movable frame 44 and the bearing support 54 of the stationary frame by a conventional LVDT motion sensor including a stationary core 160 and a movable rod 162.

The foregoing description of the invention has been directed in primary part to a particular preferred embodiment and method in accord with the requirements of the patent statutes and for purposes of explanation and illustration. It will be apparent, however, to those skilled in the art that many modifications and changes in the specifically described apparatus and method may be made without departing from the scope and spirit of the invention. For example, in an alternative embodiment, one or more other flexural or torsional bearings, e.g., flexural pivots, may be substituted for cross-spring pivots 20 in rheometer 10. Further, the motion imparted to the bob 60 and transferred to the movable frame 44 may be detected by any conventional means, including visual observation. Accordingly, those skilled in the art will appreciate that many substitutions and modifications may be incorporated in the illustrated device. Therefore, the invention is not restricted to the particular form of construction illustrated and described, but covers all modifications which may fall within the scope of the following claims.

It is Applicant's intention is the following claims to cover such modifications and variations as fall within the true spirit and scope of the invention.

What is claimed is:

1. An apparatus useful for measuring the viscosity of a liquid, comprising:
    a stationary frame;
    a tubular sleeve;
    means for suspending said tubular sleeve from said stationary frame;
    means for rotating said sleeve;
    a cylindrical bob suspended along its axis in said sleeve, said bob capable of limited angular motion about the axis of said sleeve, the radius of said cylindrical bob approximating but being less than the interior radius of said sleeve near said bob;
    a movable frame suspending said bob within said sleeve, said movable frame capable of limited angular motion in response to the motion of said bob;
    a flexural bearing suspending said movable frame from said stationary frame;
    means for positioning said bob and said sleeve so that said bob and the portion of said sleeve near said bob are capable of being immersed in said liquid; and
    means for measuring the motion of said movable frame relative to said stationary frame.

2. The apparatus of claim 1 wherein said flexural bearing is a flexural pivot.

3. The apparatus of claim 1 wherein said flexural bearing is a cross-spring pivot.

4. An apparatus useful for measuring the viscosity of a fluid, comprising:
    a stationary frame;
    a sleeve suspended from said frame;
    means for rotating said sleeve;
    a bob suspended within said sleeve, said bob capable of limited angular motion about the longitudinal axis of said sleeve;
    a flexural bearing suspending said bob from said stationary frame; and
    means for measuring the angular motion of said bob.

5. The apparatus of claim 4 wherein said bob is rigidly attached to a movable frame which is suspended from said flexural bearing.

6. The apparatus of claim 5 wherein said means for measuring comprises means for measuring the motion of said movable frame relative to said stationary frame.

7. The apparatus of claim 4 wherein said means for measuring is an electrical means for measuring motion.

8. The apparatus of claim 4 wherein the exterior contour of said bob closely approximates the interior contour of said sleeve near said bob.

9. The apparatus of claim 4 wherein said flexural bearing is a flexural pivot.

10. The apparatus of claim 4 wherein said flexural bearing is a cross-spring pivot.

11. The apparatus of claim 4 wherein said bob is suspended from a plurality of flexural bearings.

12. The apparatus of claim 11 wherein one of said flexural bearings is a flexural pivot.

13. The apparatus of claim 11 wherein one of said flexural bearings is a cross-spring pivot.

14. An apparatus useful for measuring the viscosity of a fluid, comprising:
    a stationary frame;
    a sleeve suspended from said frame;
    means for rotating said sleeve;
    a bob suspended within said sleeve, said bob capable of limited angular motion about the longitudinal axis of said sleeve;
    a torsional bearing suspending said bob from said stationary frame; and
    means for measuring the angular motion of said bob.

* * * * *